(12) United States Patent
Sutter

(10) Patent No.: US 6,932,815 B2
(45) Date of Patent: Aug. 23, 2005

(54) COAGULATION CLAMP

(75) Inventor: Hermann Sutter, Gundelfingen (DE)

(73) Assignee: Sutter Medizintechnik GmbH, Freiburg (DE)

( * ) Notice: Subject to any disclaimer, the term of this patent is extended or adjusted under 35 U.S.C. 154(b) by 169 days.

(21) Appl. No.: 10/618,110

(22) Filed: Jul. 11, 2003

(65) Prior Publication Data

US 2004/0073208 A1 Apr. 15, 2004

(30) Foreign Application Priority Data

Jul. 11, 2002 (DE) .......................................... 102 31 369

(51) Int. Cl.[7] .............................................. A61B 18/18
(52) U.S. Cl. ....................................................... 606/41
(58) Field of Search ..................................... 606/27–52

(56) References Cited

U.S. PATENT DOCUMENTS

| 4,616,953 A | 10/1986 | Gomes |
| 5,697,949 A | 12/1997 | Giurtino et al. |

FOREIGN PATENT DOCUMENTS

| GB | 2 047 791 | 12/1980 |
| WO | 00/47124 | 8/2000 |

*Primary Examiner*—Roy D. Gibson
*Assistant Examiner*—Pete Vrettakos
(74) *Attorney, Agent, or Firm*—Volpe and Koenig, P.C.

(57) ABSTRACT

A coagulation clamp (1) has clamp jaws (4) and two projections (2b or 2c, 2d) that impinge on these jaws directly or indirectly and that can be pivoted relative to one another on a common joint (2) with the aid of hand grips (3). The projections are insulated in the area of the joint and each connected directly or indirectly with a high-frequency terminal (HF). Here, the joint openings (6) are coated with an insulation that surrounds the joint axle (7) in the position of use, this insulation usefully being formed by a respective insulating sleeve (8). The joint axle (7) is made up of a sleeve (71) and an insert (72) that can be placed therein in telescoping fashion and that has a press-fit seating and that, on the side of sleeve (71) facing away from the insertion side, extends up to or into an opening (9a) of a termination (9) of this sleeve (71) and is fixedly connected with this sleeve termination (9), preferably being welded thereto. This results in a stable joint (2) that can absorb large forces. Because both the sleeve (71) and its insert (72) can protrude past the clamp jaw (4) externally with a respective stop or flange (12 or 13), lateral or shear forces can also be absorbed effectively.

9 Claims, 3 Drawing Sheets

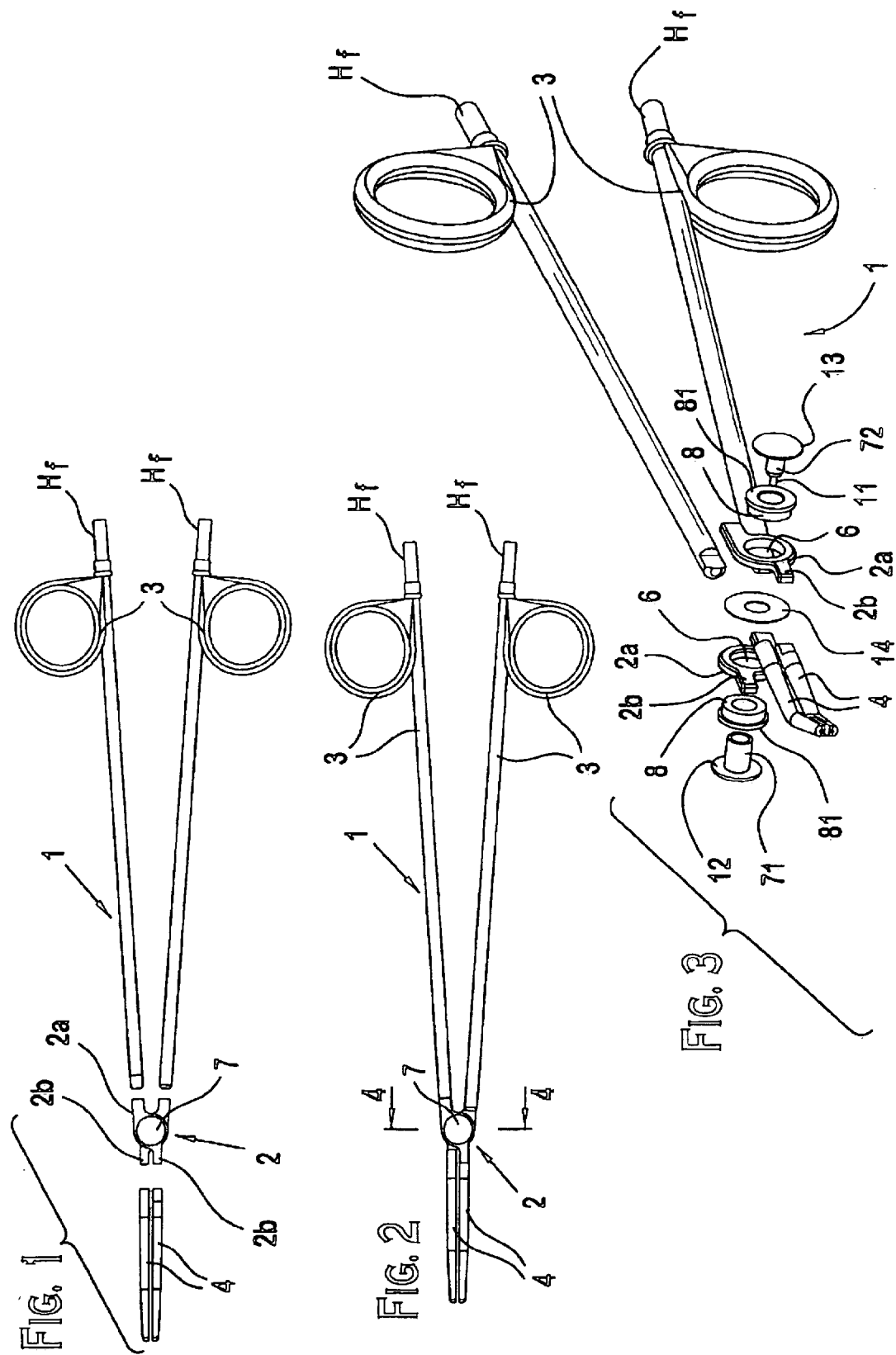

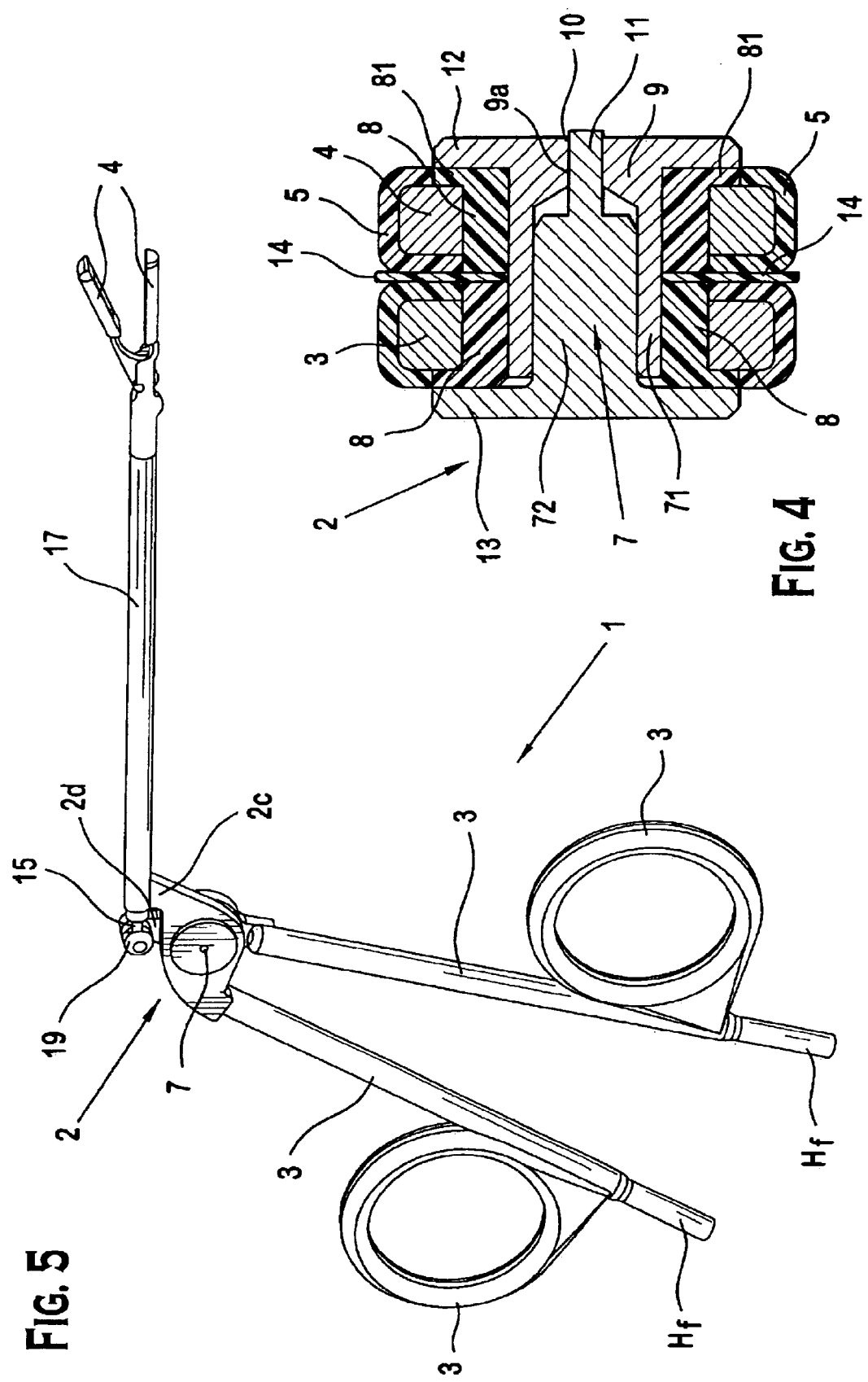

COAGULATION CLAMP

BACKGROUND

The present invention relates to a coagulation clamp having clamp jaws and having two projections that load the jaws directly or indirectly and that can be pivoted relative to one another at a common joint with the aid of hand grips, said projections being coated or covered at least partly with insulating material in the area of the joint, and each being connected directly or indirectly with a high-frequency terminal and insulated from one another in the joint, and the projections are situated near the joint openings, through which a joint axle or runs.

Such coagulation clamps are known. As a rule, the high-frequency terminals are provided at the hand grips. As an axle for the joint, a screw provided with an insulating coating is often used with which the two clamp jaws are also fastened to one another in pivotable fashion at their hand grips. Due to the pivoting motions executed during use, the insulating coating of the joint axle can be damaged, and this can make the coagulation clamps unusable.

Various types of clamps are typically used. Tube-shaft clamps or pincers are used for endoscopic operations, and pincers having jaws are used in open surgical applications. The demands made on the joint in these different types of pincers or clamps are various. In endoscopic clamps, the pressure that can be applied to the joint is lower, and lateral shear forces rarely occur.

In the clamps having jaws for open surgery, the pressure that can be applied to the joint through the lever action of the relatively long grip leg and the long front part is higher. In addition, there is also the possibility of working laterally and exerting a lateral pressure or pulling, so that shear forces occur in the joint that must be intercepted by the construction in order to avoid a loosening of the joint.

Bipolar forceps have also long been known, and have proven their worth in situations of coagulation, in particular in the closing of bleeding vessels during operations in all types of surgery. The problem of an insulated joint axle whose insulation can become damaged over the course of time, in particular if shear forces also occur, does not exist here, because the forceps jaws are each pivoted against the force of a spring. However, due to the spring tension that is predetermined in these forceps jaws, they are not suitable for the execution of spreading motions at the operating location during preparation. In such a forceps, an individual spreading pressure cannot be exerted by hand. Thus, for a preparation additional instruments are required; that is, under certain circumstances a repeated change of instruments must take place between preparation instruments and bipolar forceps. If areas of tissue having a high density of vessels are involved, such as tonsils or thyroid glands, a very high degree of bleeding can take place. In order to handle this adequately, it is useful to suction off the emerging blood, in order to allow the bleeding area to coagulate in a well-directed manner.

SUMMARY

The underlying object of the present invention is therefore to create a coagulation clamp of the type cited above that is suitable both for spreading or preparation and also for coagulation, in which the insulation of the two clamp jaws in the joint area is improved, and that is largely insensitive to damage due to the pivoting movements, and in which joint shear motions can also be transmitted.

In order to achieve this object, the coagulation clamp defined above is provides that the joint openings are covered with an insulation that surrounds the joint axle in the position of use, and that the joint axle is made up of a sleeve and an insert that can be placed therein in telescoping fashion, which insert extends, on the side of the sleeve facing away from the insertion side, up to or into an opening of a termination of the sleeve, or protrudes past this termination at the end face thereof, and is fixedly connected or welded with this sleeve termination.

This results in a compact joint that, due to the telescoping construction of the joint axle, can compensate dimensional tolerances without problems, in particular with respect to the width of the insulated projections, and can nonetheless transmit high forces, including shear forces. Here, a solid connection of the sleeve and its insert that can be placed therein, and can be screwed in if necessary, and can be moved therein in telescoping fashion, is provided in the axial direction as well, so that the stability of the joint is correspondingly long-lasting.

For the assembly and the handling, it is especially useful if the insert that can be placed in the sleeve has at its front end in the direction of insertion a cross-sectional reduction that extends into a correspondingly dimensioned opening of the termination of the sleeve, or passes through this opening. Thus, practically speaking, in the direction of insertion the insert has a pin having a smaller cross-section that can be introduced correspondingly well into a mating opening and fits therein, in particular if in the interior of the sleeve there is provided a funnel or cone, leading to the termination of the sleeve, as a guide surface for this pin. After the pressing together of the sleeve and its insert, which already effects a connection of these two parts, the mentioned welding, e.g. a laser welding, can additionally be carried out.

A construction of the present invention that offers significant advantages can be provided in that the sleeve that forms the joint axle can have, at its end surface having the termination, a radially protruding stop or flange for overlapping a clamp jaw that is adjacent in this area, and the insert that can be introduced in telescoping fashion into the sleeve can likewise have, on its rear end in the direction of insertion, a stop or flange for impinging on or overlapping the other jaw of the coagulation clamp, and the two jaws of the coagulation clamp can be held between the stops or flanges in the position of use. This also results, in a simple manner, in an axial stabilization of the overall joint. Through the telescoping joining of the sleeve and its insert alone, the projections between the stops or flanges are defined in the axial direction, and dimensional tolerances regarding the thickness of the projections and the insulation thereof are automatically compensated in that the insert is introduced and clamped more or less deeply into the sleeve, and nonetheless can also be connected, screwed or welded to the termination thereof In a further, highly significant construction of the present invention, it can be provided that in the joint area between the projections, on surfaces that can be rotated relative to one another given mutual pivoting, there is situated a glide disk or glide ring, made for example of PTFE (polytetrafluoroethylene) or of Teflon. In this way, the relative pivotability of the projections can be improved in the joint area due to reduced friction, without the danger arising of damaging the insulation. Rather, the insulating effect can be further increased by these additional glide disks, if they are made of insulating material. This glide disk also reduces the danger that the insulation of the projections will become detached when there is mutual rubbing. That is, the glide disk also increases the security against a short-circuit.

The joint openings of the projections can each be sheathed with an insulating sleeve, and the glide ring can also in particular extend between these insulating sleeves.

Due to these insulating sleeves, the joint axle, which is preferably made of metal, e.g. of steel, is securely separated and insulated from the respective insulating jaw. Here, these sleeves, which are made in particular of insulating plastic, also reduce friction, and facilitate the ability to pivot of the two projections.

A further useful construction of the coagulation clamp according to the present invention, and in particular of the joint thereof, can be that the insulating sleeves each have, externally, a widened edge on which the stops or flanges of the sleeve, or of the insert that can be introduced into the sleeve, can lie in the position of use. In this way, the insulating material of the insulating sleeves is also situated on the outside of the joint between the projections and of the pivot axle, or the stops of this pivot axle, and improves the insulating effect.

The clamp jaws of the coagulation clamp according to the present invention can each be connected directly to one of the projections, or can be formed as the continuation thereof. Another constructive possibility is a one-piece construction of the respective projection and the associated clamp jaw.

In a specific embodiment of the present coagulation clamp, formed with a knee bend, it is advantageous if one of the clamp jaws is connected directly or indirectly with one of the projections via a pull rod. Here the pull rod can be mounted in movable fashion on one of the projections, in particular via a ball joint. The second clamp jaw can be angled off and connected fixedly with the other of the two projections, in particular via an extension. This second clamp jaw with its extension can act here as a mount for the pull rod with the clamp jaw fastened in movable fashion thereon. The joint between the two projections can be formed in the manner previously described, and thus produces, even in a specific embodiment having a knee bend, a connection of the joint body having long-term stability.

Due to the insulating sleeves, having on the external side a widened edge that overlaps the projections, the jaws of the coagulation clamps can be free of the insulating covering in the joint area, at the location of the respective insulating sleeve, and this can hold as well for the inside of the joint opening. In this way, above all the locations on the projections that are exposed to friction and relative motion in the joint area are not protected only with an insulating coating that may be able to be rubbed off; rather, the respective insulating sleeve, having its relatively high degree of durability and long life span, is situated at these points.

Above all, the features and measures described above, individually or in combination, result in a stable and nonetheless smooth-acting joint whose metal parts are joined in telescoping fashion in a press-fit. At the same time, the protruding edges or flanges form an outer guide of the joint, so that shear forces in the lateral direction can also be absorbed. Here, a pin on the insert is preferably guided through a centric bore in the termination of the sleeve, so that after the pressing together of the sleeve forming the joint and the insert, and after the adjustment of the instrument for an easy movement without play, this pin can additionally be fixed with a welding point or laser point. In this way, there arises a compact joint that also fixedly surrounds the insulating sleeves in the joint openings of the clamp jaws. The projections, the clamp jaws, and the front parts are here coated with powder in order to provide insulation. Because the layer thickness can fluctuate, tolerances are unavoidable, but these can be compensated by pressing together the sleeve and the insert in telescoping fashion. This compensation of tolerances is further improved by the insulating disk or glide disk, through which it can additionally be achieved that the guiding of the joint in the interior is improved, and the insulated parts of the clamp jaw do not rub directly against one another when the clamp is actuated.

A further advantage of this combination of features is that the corresponding joint can be used both in embodiments having knee bends and in straight embodiments of the coagulation clamp. There thus results a flexible and economical production of different types or models of coagulation clamps having short or long hand grips and short or long front parts and differently shaped grasping surfaces, according to the purpose of the operation.

BRIEF DESCRIPTION OF THE DRAWINGS

In the following, exemplary embodiments of the present invention are explained in more detail on the basis of the drawings. The following are shown in partly schematic representation:

FIG. 1 shows a side view of a coagulation clamp according to the present invention for the final connection of the hand grips and the clamp jaws, or front parts, with a joint body, FIG. 2 shows a representation corresponding to that of FIG. 1, in which the coagulation clamp according to the present invention is joined and connected so as to be ready for use, FIG. 3 shows an exploded view of the coagulation clamp shown in FIGS. 1 and 2, in particular having the individual parts forming the joint in a simultaneous perspective view, FIG. 4 shows, in an enlarged scale, a section according to the line A—A in FIG. 1 through the joint, with insulating sleeves covering the respective joint opening, a glide disk situated between these, and metal parts that engage in one another in telescoping fashion and that form the joint axle, FIG. 5 shows a perspective view of a further coagulation clamp according to the present invention in a knee-bend embodiment, having a tube shaft and a pull rod used for the actuation of a clamp jaw.

DETAILED DESCRIPTION OF THE PREFERRED EMBODIMENTS

Figure 6:
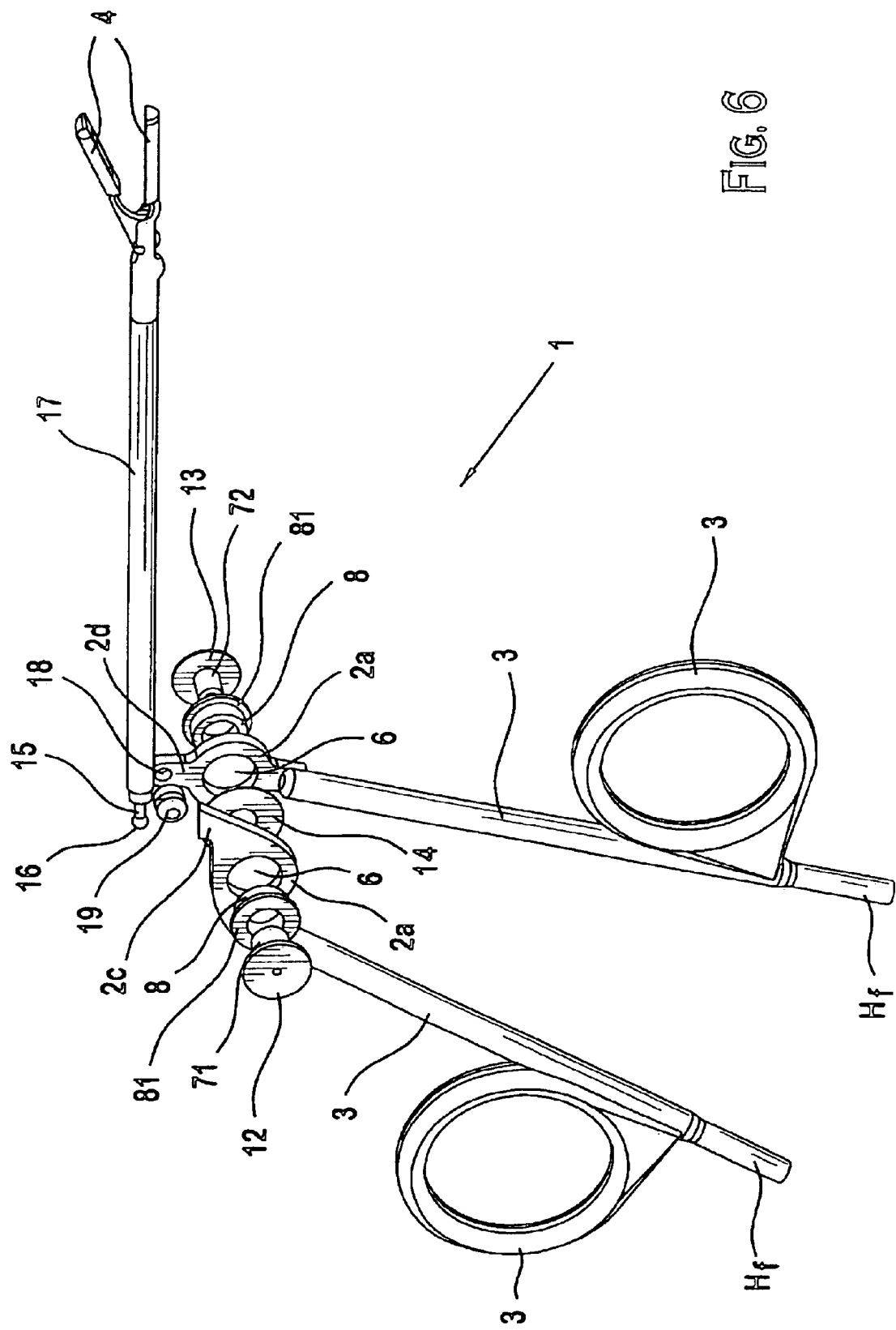
FIG. 6 shows an exploded view of the coagulation clamp shown in FIG. 5, in particular with the individual parts forming the joint, in a simultaneous perspective view.

A coagulation clamp designated as a whole as 1 has two front parts or clamp jaws 4 that can be pivoted relative to one another on a common joint 2 with the aid of hand grips 3, each of these front parts or clamp jaws having a high-frequency terminal HF. Here, these parts made up of hand grip 3 and clamp jaw 4 are insulated from one another in joint 2, and also adjacent thereto.

In FIG. 4, it can be seen that clamp jaws 4 and hand grip parts 3 are also partially coated or covered with insulating material 5 in the joint area on a joint body 2a; this can be achieved by a powder coating.

Above all, in FIG. 4 it is shown that joint openings 6 (visible in FIG. 3) of clamp jaws 4 or of joint 2 are covered with an insulating sleeve 8 that in the position of use surrounds joint axle 7 (described below), which passes through these openings.

Here, according to FIGS. 3 and 4 joint axle 7 is made up of a sleeve 71 and an insert 72 that can be placed therein in telescoping fashion and fixed therein by a press fit; FIG. 3 shows the not-yet-assembled arrangement and FIG. 4 shows the assembled arrangement.

In the assembled position according to FIG. 4, insert 72 extends, on the side of sleeve 71 facing away from the side of insertion, into an opening 9a of a termination or base 9 of sleeve 71, and in the exemplary embodiment protrudes past this termination 9 at its end surface, and is fixedly connected therewith, even having a welding point 10.

Here, the insert 72 that can be placed in the sleeve 71 has on its front end in the direction of insertion a cross-sectional reduction in the form of a pin 11 that extends into correspondingly dimensioned opening 9a of termination 9 of sleeve 71, and also passes through this opening in the exemplary embodiment. However, this insert could also end already inside opening 8, and could likewise additionally be welded and/or screwed in there.

Sleeve 71, which is associated with joint axle 7 and contributes to its formation, has on its end face having termination 9 a radially protruding stop or flange 12 for overlapping a clamp jaw 4 that is adjacent in this area. Likewise, insert 72 that can be introduced in telescoping fashion into sleeve 71 has on its back end in the direction of insertion a stop or flange 13 for impinging on and overlapping the other clamp jaw 4 or grip part 3 of coagulation clamp 1, so that both grip parts 3 or clamp jaws 4 of coagulation clamp 1 are held axially in the position of use on joint 2 between stops or flanges 12 and 13. Due to the fact that sleeve 71 and insert 72 can be joined in telescoping fashion, dimensional tolerances that occur in the axial direction due to insulation 5 can also be easily compensated during assembly, because welding point 10 is attached only after the dimensionally correct joining has taken place. In the joint area, moreover, a glide disk 14 or a glide ring, made for example of insulating material or plastic, is situated between surfaces that can rotate relative to one another during mutual pivoting; this can be seen both in FIG. 3 and, in the position of use, in FIG. 4. Its radial extension is dimensioned such that it also extends between the insulating sleeves 8 that cover joint openings 6, as is shown clearly in FIG. 4. The inner opening of glide disk 14 corresponds in its diameter to the outer diameter of sleeve 71, which belongs to joint axle 7. On the other hand, glide disk 14 also extends radially to approximately the outside of insulated clamp jaws 4.

Moreover, in FIG. 4 it can be seen clearly that insulating sleeves 8 each have on the outside a widened edge 81 on which stops or flanges 12 and 13 of sleeve 71, or of insert 72 that can be introduced into this sleeve, can lie externally, so that at this location as well the best possible insulation is achieved between metallic clamp jaws 4 and the metallic parts of joint axle 7.

Here it is additionally provided that the projections (2b or 2c, 2d) and/or clamp jaws (4) of coagulation clamp 1 are free of insulating coating 5 in the joint area and in the area of their joint opening 6, at the point at which the respective insulating sleeve 8 works therewith.

FIGS. 5 and 6 show an embodiment of coagulation clamp 1 having a knee bend, in which a tubular extension or a tube shaft 17 of the one clamp jaw 4 is fastened to projection 2c at an angle to hand grip 3. Projection 2d has a bore 18 in which a cylindrical receiving part 19 provided with a peripheral slot is mounted. The other clamp jaw 4 is connected with a pull rod 15 that runs in the interior of tube shaft 17 and that has a spherical abutment 16 on the end facing away from the clamp jaw. Abutment 16 of pull rod 15 engages in the slot of receiving part 19, and is mounted there in movable fashion. Clamp jaw 4, fastened to the outer end of the pull rod, is connected in pivotable fashion with the second clamp jaw or with the end of tube shaft 17.

A coagulation clamp 1 has clamp jaws 4 and two projections 2b or 2c, 2d that impinge on these jaws directly or indirectly and that can be pivoted relative to one another on a common joint 2 with the aid of hand grips 3, these projections being insulated in the area of the joint and each connected directly or indirectly with a high-frequency terminal HF. Here, joint openings 6 are coated with an insulation that surrounds joint axle 7 in the position of use, this insulation usefully being formed by a respective insulating sleeve 8. Joint axle 7 is made up of a sleeve 71 and an insert 72 that can be placed therein in telescoping fashion and that has a press-fit seating and that, on the side of sleeve 71 facing away from the insertion side, extends up to or into an opening 9a of a termination 9 of this sleeve 71 and is fixedly connected with this sleeve termination 9, preferably being welded thereto. This results in a stable joint 2 that can absorb large forces. Because both sleeve 71 and its insert 72 can protrude past clamp jaws 4 externally with a respective stop or flange 12 or 13, lateral or shear forces can also be absorbed effectively.

What is claimed is:

1. A coagulation clamp (1) comprising clamp jaws (4) and having two projections (2b or 2c, 2d) that impinge on the clamp jaws directly or indirectly and that can be pivoted relative to one another at a common joint (2) via hand grips (3), the projections being coated or covered at least partly with insulating material (5) in an area of the joint, and each being connected directly or indirectly with a high-frequency terminal (HF) and insulated from one another in the joint (2), and the projections being situated adjacent to joint openings (6), through which a joint axle (7) runs, the joint openings (6) are covered with an insulation that surrounds the joint axle (7) in a position of use, and the joint axle (7) includes a sleeve (71) and an insert (72) located therein in telescoping fashion, the insert (72) extending, on a side of the sleeve (71) facing away from an insertion side, up to or into an opening (9a) of a termination (9) of the sleeve (71), or protruding past the termination at an end face thereof, and being fixedly connected or welded with the sleeve termination (9).

2. The coagulation clamp as recited in claim 1, wherein the insert (72) placed in the sleeve (71) has on a front end thereof in a direction of insertion a cross-sectional reduction (11) that extends into a correspondingly dimensioned opening (9a) of the termination (9) of the sleeve (71), or passes through the opening.

3. The coagulation clamp as recited in claim 1, wherein the sleeve (71) forming the joint axle (7) has on an end face comprising the termination (9) a radially protruding stop or flange (12) for overlapping one of the projections (2b or 2c, 2d) that is adjacent in this area, and the insert (72) introduced in telescoping fashion into the sleeve (71) also has on a rear end thereof in a direction of insertion a stop or flange (12) for impinging on an other one of the projections of the coagulation clamp (1), and the two projections (2b or 2c, 2d) of the coagulation clamp (1) are held between the stops or flanges (12, 13) in a position of use.

4. The coagulation clamp as recited in claim 1, further comprising a glide disk (14) or a glide ring made of polytetrafluoroethylene or Teflon situated in an area of the joint between the projections (2b or 2c, 2d), on surfaces that can be rotated relative to one another when there is a mutual pivoting.

5. The coagulation clamp as recited in claim 4, wherein the joint openings (6) are each covered by an insulating sleeve (8), and the glide ring extends between these insulating sleeves (8).

6. The coagulation clamp as recited in claim 5, wherein the insulating sleeves (8) each have a widened edge (81) on an outside thereof, on which stops or flanges (12, 13) of the sleeve (71), or of the insert (72) that can be introduced into the sleeve, lie in the position of use.

7. The coagulation clamp as recited in claim 1, wherein the clamp jaws (4) are each connected directly with one of the projections (2b or 2c, 2d), or are formed as the continuation thereof.

8. The coagulation clamp as recited in claim 1, wherein one of the clamp jaws (4) is connected directly or indirectly with one of the projections (2c, 2d) via a pull rod (15).

9. The coagulation clamp as recited in claim 1, wherein the projections (2b or 2c, 2d) and/or clamp jaws (4) of the coagulation clamp (1) in an area of the joint are free of the insulating coating (5), in an area of the joint opening (6) at a location of the respective insulating sleeve (8).

* * * * *